US00PP24373P2

(12) United States Plant Patent
Sparks

(10) Patent No.: US PP24,373 P2
(45) Date of Patent: Apr. 8, 2014

(54) PECAN TREE NAMED 'CUNARD'

(50) Latin Name: *Carya illinoinensis*
Varietal Denomination: Cunard

(75) Inventor: Darrell Sparks, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 266 days.

(21) Appl. No.: 13/199,810

(22) Filed: Sep. 8, 2011

(51) Int. Cl.
*A01H 5/00* (2006.01)

(52) U.S. Cl.
USPC ..... Plt./153

(58) Field of Classification Search
USPC ..... Plt./153
See application file for complete search history.

*Primary Examiner* — Kent L Bell
(74) *Attorney, Agent, or Firm* — Klarquist Sparkman, LLP

(57) ABSTRACT

A pecan tree distinguished by the following unique combination of characteristics: Precociousness and prolificacy, early nut maturity, large nut size, a nut with a high kernel percentage, good kernel color, lack of speckling and a good resistance to leaf scab.

5 Drawing Sheets

Latin name of the genus and species of the plant: *Carya illinoinensis.*

Variety denomination: 'Cunard'.

BACKGROUND OF THE INVENTION

The present invention relates to a new and distinct variety of pecan tree named 'Cunard'. My new tree can be used in gardens or for commercial production of pecan nuts. This new tree was selected from seedlings grown from controlled pollination in Watkinsville, Ga. in 1989. The 'Cunard' selection resulted from crossing 'Wichita' (unpatented) as the seed parent with 'Pawnee' (unpatented) as the pollen parent. The resulting tree was selected when growing in a cultivated area at Watkinsville, Ga.

BRIEF SUMMARY OF THE INVENTION

'Cunard' is distinguished from other pecan varieties known to the inventor due to the following unique combination of characteristics: High precocity and prolificacy, early nut maturity, large nut size, a nut with a high kernel percentage, good kernel color and absence of speckling, and good resistance to scab disease (*Fusicladosporium effusum*), black pecan aphid (*melanocallis caryaefoliae*), pecan leaf scorch mite (*eotetranychus hicoriae*), and N scorch.

Asexual reproduction of my new 'Cunard' variety by grafting, (topworking) onto 'Kiowa' (unpatented) pecan trees in 2002 at a location in Leary, Ga. and in 2007 in Albany, Ga., was performed in order to evaluate these trees. Asexual propagation of 'Cunard' pecan trees has also been performed at other locations in Georgia. Asexual reproduction of my new 'Cunard' variety has shown that the forgoing characteristics come true to form, are firmly fixed, and are established and transmitted through succeeding propagations.

The following detailed description is of the original tree and of asexually reproduced progeny growing in Albany, Ga.; Leary, Ga.; Lakeland, Ga. and Watkinsville, Ga.

Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to The Royal Horticultural Society (R.H.S.) Colour Chart, 2001. The colors of an illustration of this type may vary with lighting and other conditions. Therefore, color characteristics of this new variety should be determined with reference to the observations described herein, rather than from these illustrations alone.

DETAILED DESCRIPTION

BOTANICAL

The following detailed description of 'Cunard' is based on observations of the original tree in Watkinsville, Ga. and of asexually reproduced progeny growing in Albany, Ga. and Leary, Ga.

Varietal name: 'Cunard'.

Parentage:

*Seed parent.*—'Wichita'.

*Pollen parent.*—'Pawnee'.

Tree:

*Overall shape.*—Upright, moderately spreading, height to width ratio is about 1:1.

Figure 1:
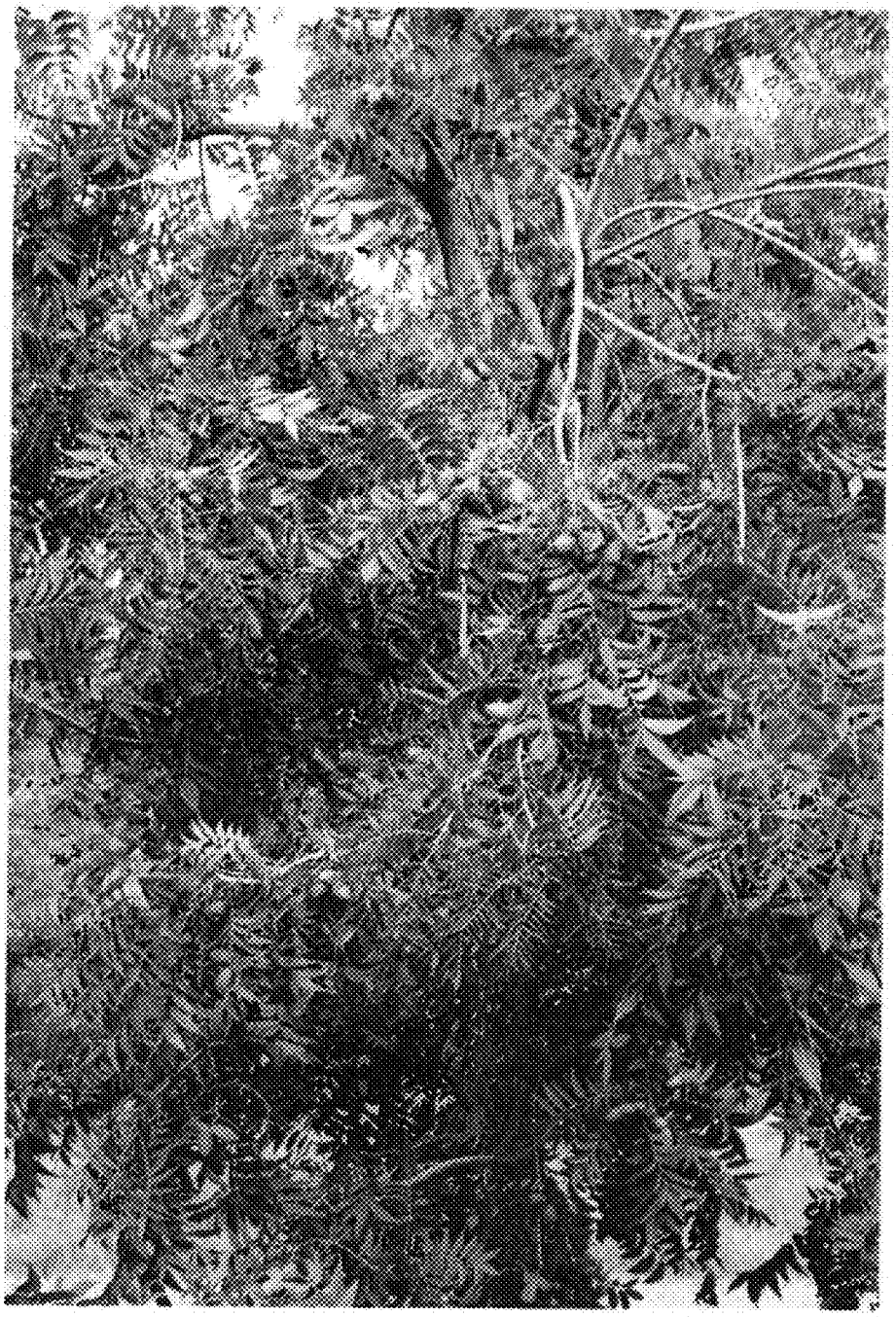
FIG. 1 is a photograph showing a seven-year old 'Cunard' tree with limbs bent by the weight of the fruit.
Figure 2:
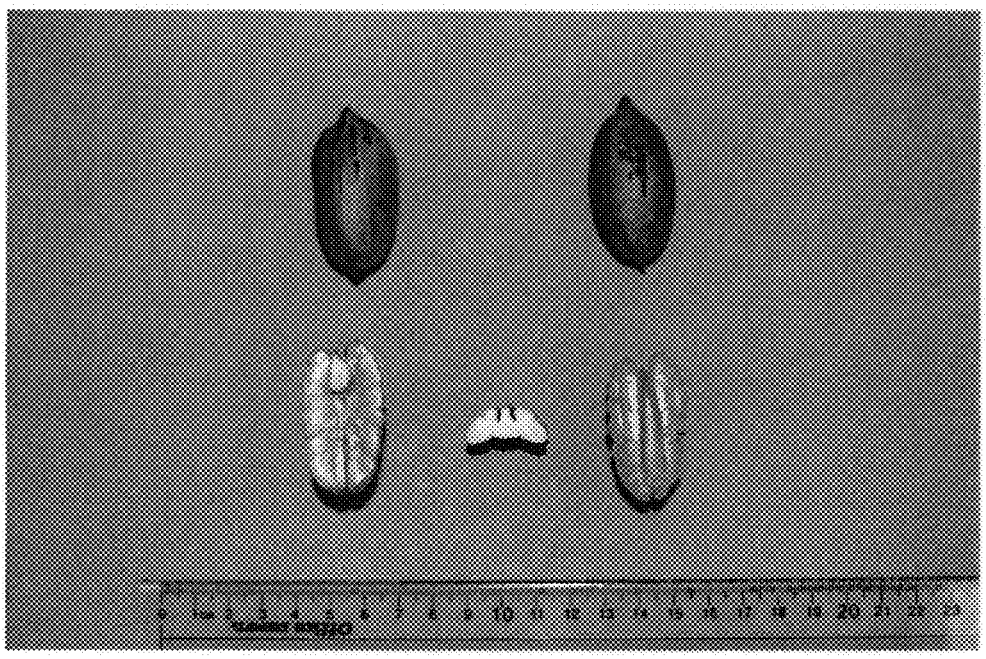
FIG. 2 is a photograph showing nuts and kernels of 'Cunard'; with the nut suture side shown on the top left and the nut non-suture side being shown on the top right; with the ventral side of the kernel shown at the lower left, a cross-section of the kernel being shown at the lower middle, and the dorsal side of the kernel being shown at the lower right.

*Vigor.*—Vigorous, precocious, 'Cunard' fruited the second year after grafting (topworking) onto 'Kiowa' trees (see Table 5), and has done so in subsequent years. 'Cunard' is also prolific (see the fruit-laden tree in FIG. 1). The original tree fruited 8 years from seed.

*Height.*—Of original tree, about 13.4 meters.

*Width.*—Of original tree, about 12.5 meters.

*Trunk.*—Of original tree (measured 12 cm above ground level) about 52.0 cm in diameter.

*Trunk bark texture.*—Fissured.

*Trunk bark color.*—Grey-Brown (RHS 201 C).

*Patches.*—Trunk has no markings.

*Shoot color.*—Shoots in woody stage are Grey-Brown (RHS 199 A) in color, with Light Green lenticels (RHS 144 B) that are elongated and about 1 mm long by 0.05 mm wide. Lenticels are oval shaped. There are about 35 lenticels per square cm.

*Internodes.*—Average internode length is about 0.9 cm between the $3^{rd}$ and $4^{th}$ leaf.

*Bearing.*—Thus far consistent each year.

*Disease and insect resistance.*—Good resistance to scab (*Fusicladosporium effusum*) [see Table 7]. Excellent resistance to black pecan aphid (*Melanocallis caryaefoliae*) (Table 9), good resistance to pecan leaf scorch mite (*eotetranychus hicoriae*) (Table 8), and excellent resistance to N scorch (Table 10).

Leaves: The mature leaf is odd pinnate compound, deciduous with leaflets having a dark green upper surface and a lighter green lower surface. Each mature leaf has from 11 to 17 leaflets. Opposite leaflets are oriented at 180 degrees relative to each other. This flat orientation is most pronounced on basal leaflets with the leaflets becoming somewhat convoluted on apical leaflets.

*Size of mature leaf.*—14.2 cm long, 17.7 cm wide.

*Petiole.*—Oval shape in cross-section, pale green in color (RHS 144 B). The length of the petiole of the fourth leaf from the base is about 4.1 cm. The diameter of the petiole at the fourth leaf from the base is about 2.1 mm.

*Leaflet.*—Size and shape: One leaflet from fourth pair from the base: 9.4 cm long by 2.4 cm wide. Elliptic in shape. Apex acuminate and narrow. Base oblique. Margin serrate. Undulation of leaflet margins is absent on basal leaves, but increases from basal to apical leaves. Texture: Upper and lower surface is glabrous. Sheen: Upper surface is glossy; lower surface is non glossy. Petiole: Length: Typical 5 mm; Diameter: Typical 0.5 mm; Yellow-green (RHS 145 C). Margin: Serrate. Tip shape: Acuminate. Leaflet color: Upper leaf surface: Green (RHS 137 A). Lower leaf surface: Green, slightly lighter in color than upper surface (RHS 137 B). Pubescence: Upper and lower leaflet surface is glabrous. The length, width, thickness and other measurements were obtained from observations of a typical leaf.

Inflorescence:

*General.*—The 'Cunard' pecan is monoecious, and anemophilous. Dichogamy is protogynous, pollinated by 'Cheyenne' (unpatented), 'Desirable' (unpatented) and 'Pawnee' (unpatented). 'Cunard' will pollinate its pollinizers (see Table 1).

*Flowers.*—Pistillate flowers are borne on a determinate spike, with staminate flowers borne on a determinate pendulous catkin. 4-6 individual pistillate flowers per spike, borne alternately on terminally-positioned spikes. Spike lengths: Typical 7.3 cm; spike diameter without fruit cluster: Typical 3 mm; spike diameter with fruit cluster: Typical 13 cm; spike color: Yellow-green (RFH 145 C). The pistillate flower is symmetrical with no stamens or petals. Pedicel: None. The staminate or catkin length is 160 mm and width is 6 mm. The staminate color is green (RHS 144 B) with gold pollen (RHS 3 A). The involucre size, which includes the stigma, is 7.5 mm long by 1.8 mm wide. The flower has one pistil with a green (RHS 144 B) stigma. The flower has four bracts, which are Green (RHS 144 B), linear, lanceolate, 3.8 mm long by 0.5 mm wide and are fused at the bases, forming a copular involucre.

Fruit: Has fruited consistently thus far. In some years, the crop will require fruit thinning.

*Mature fruit.*—Is dehiscent.

Figure 4:
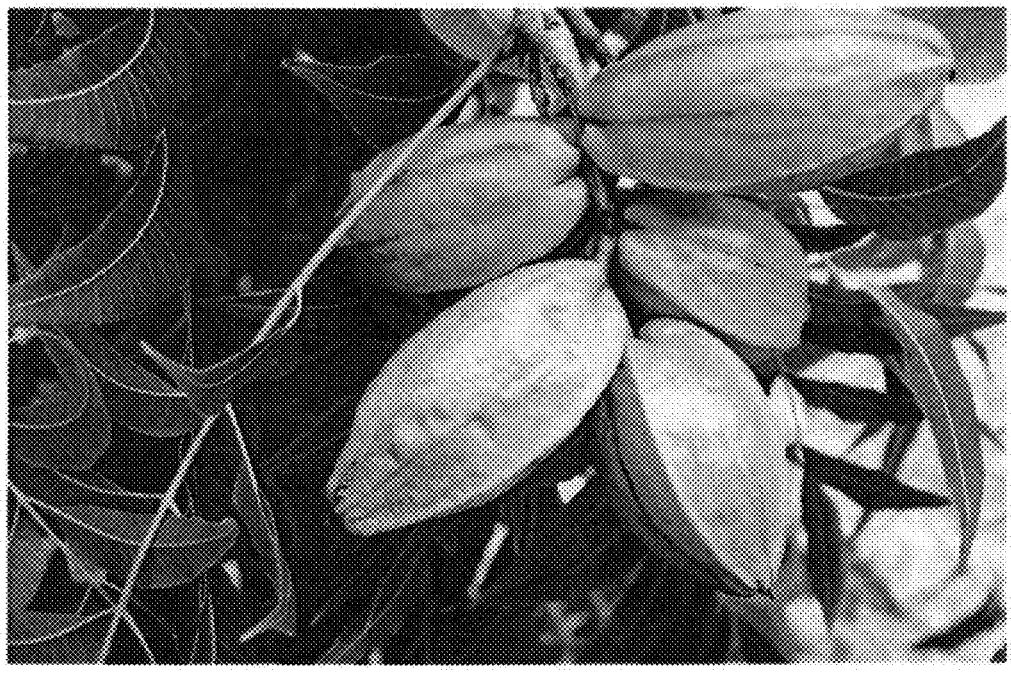
FIG. 4 is a photograph showing a fruit cluster of 'Cunard' pecans and portions of some leaves.

*Shuck.*—Pale Green (RHS 144 B), surface has subtle indentations (see FIG. 4).

*Shuck shape.*—Oval. Shuck length: Typical 6.3 cm. Shuck diameter: Typical 3.1 cm.

*Fruit splits.*—During the water stage (liquid endosperm stage), but typically is less than 10 percent.

Figure 5:
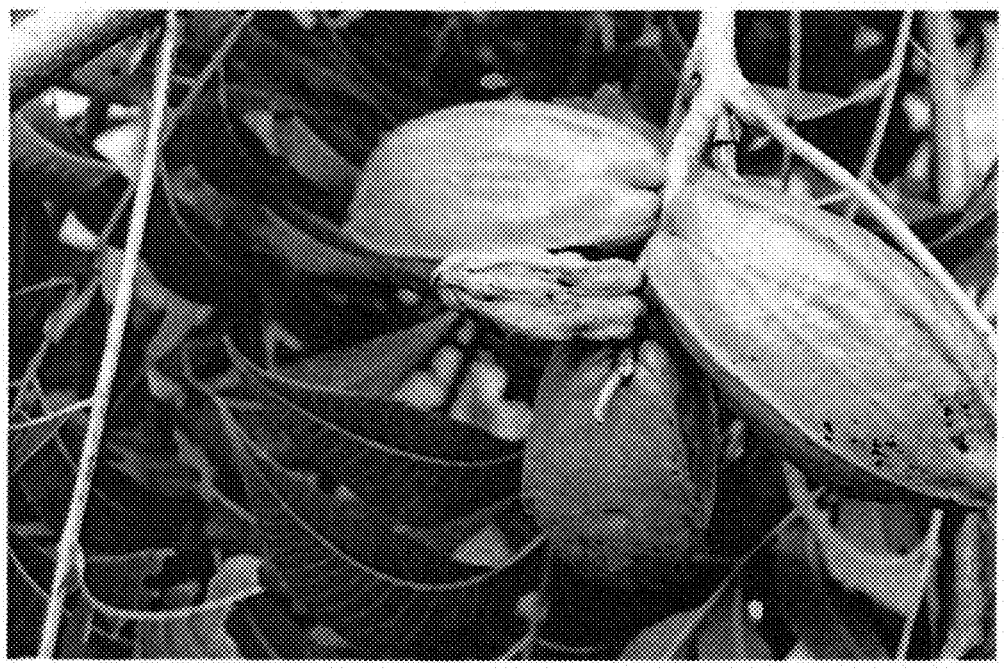
FIG. 5 is a photograph of a cluster of fruit with one rudimentary fruit a "pop" (the kernel has not developed and the shuck will fail to dehisce). 'Cunard' produces a low percentage of rudimentary fruit, typically less than five percent.

*Fruit cluster.*—About three fruits per cluster typical (Table 6), occasionally a fruit cluster will have one rudimentary fruit (FIG. 5).

Nuts: (Observations from typical nuts from multiple growing seasons in Watkinsville, Ga. and Albany, Ga.).

*Size.*—Large, over a number of growing seasons, 48 nuts per pound in Watkinsville, Ga. and 42 nuts per pound in Albany, Ga., where irrigation was better (see Tables 2 and 3). Nut size is similar to 'Morrill' and 'Desirable', and larger than 'Byrd', 'Pawnee' and 'Stuart'. A nut size of less than 45 nuts per pound qualifies nuts for the profitable "mammoth half" trade. Length about 50.4 mm, width about 23.9 mm (width measurement taken midway along the length of the nut and across sutures); length to width ratio about 2.11. Nut flatness, (ratio of width across sutures to width between sutures) is about 1.01.

*Form.*—Obovate, cross-section shape is round, base is blunt (obtuse), apex is cuspidate to cuspidate asymmetric, with a grooved apex.

*Sutures.*—Subtle, non elevated.

*Weight.*—10.8 grams per nut (non-limiting soil moisture, average of observed nuts grown in Albany, Ga.).

*Cluster size.*—About 2.9 fruits per cluster.

*Shell surface.*—Has subtle ridges and has a rough texture.

*Shell color.*—Grey-Brown (RHS 164 A).

*Shell thickness.*—Thin, 0.73 mm.

Figure 3:
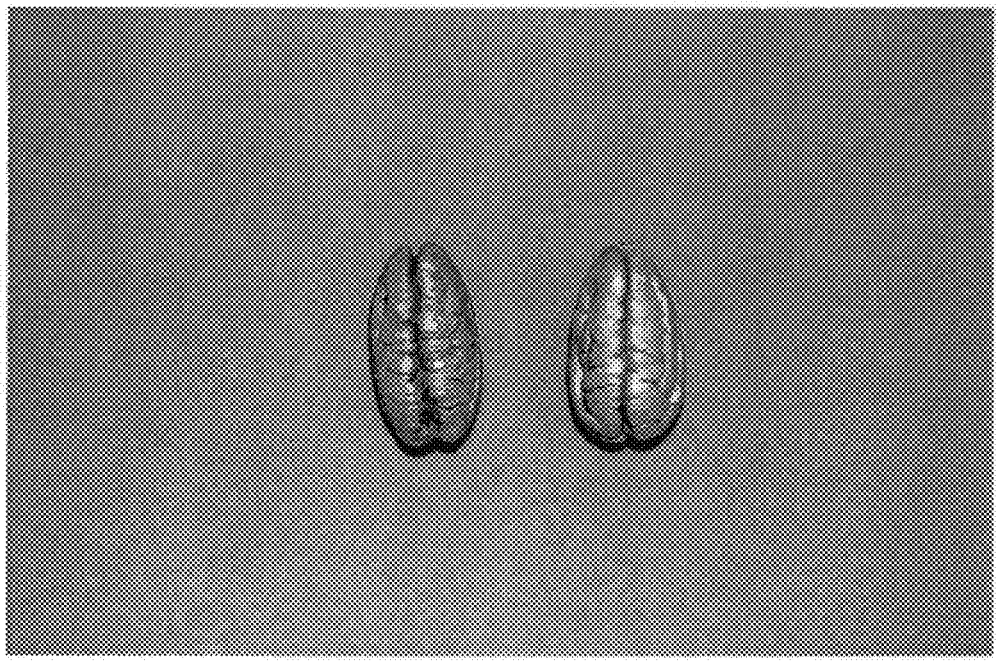
FIG. 3 is a photograph showing a 'Cunard' kernel on the left and a 'Morrill' (U.S. Plant Pat. No. 23,335) kernel on the right, and illustrating multiple tertiary grooves at right angles to the central partition wall that are present in typical 'Cunard' nuts.

*Kernel grooves.*—Multiple tertiary grooves that are at right angles to the central partition wall (see FIG. 3).

*Kernel color.*—Good color, Greyed-Orange (RHS 164 B).

*Kernel coat.*—Speckling has not been a problem (Table 4).

*Kernel shape.*—Obovate.

*Kernel length.*—Typical 3.8 cm.

*Kernel width.*—Typical 1.39 cm.

*Kernel thickness.*—Typical 0.8 cm.

*Kernel percentage of nut.*—High, about 61.5 to 63.5 percent (Tables 2 and 3). Similar to 'Byrd', less than 'Morrill', but substantially higher than 'Desirable' and 'Stuart'.

*Nut maturity.*—Early. September 27$^{th}$ on average in Watkinsville, Ga., 2000-2006, later than 'Pawnee' by about seven days and later than 'Byrd' by about five days, but earlier than 'Stuart' (unpatented) by about twelve days and 23 days ahead of 'Desirable'.

*Harvestability.*—Suitable for machine harvest.

*Shelling ability.*—Shells exceptionally well, percentage of kernels with intact halves is high. Typically, less than 5.0 percent of the kernels are chipped or broken.

*Shuck decline.*—Shuck dieback during kernel formation has not been observed to be a problem. Typically less than five percent rudimentary fruit.

COMPARISONS TO OTHER VARIETIES

'Cunard' does not have the kernel speckling problem of its male parent 'Pawnee' or the shuck decline problem of female parent 'Wichita'. Unlike 'Pawnee', 'Wichita', and 'Desirable', 'Cunard' has good resistance to the leaf scab fungus. 'Cunard' has excellent resistance to black pecan aphids and is better than in 'Byrd', 'Morrill', and 'Sumner'. Resistance to pecan leaf scorch mite is good but less than in 'Byrd' and 'Cunard'. Relative to the highly susceptible 'Desirable', resistance to N scorch is excellent and similar to 'Byrd' and 'Morrill'. Like 'Byrd' and 'Pawnee', nut maturity is early which makes 'Cunard' suitable for the premium price early market. Nut size is substantially larger than 'Byrd' and 'Pawnee' which increases the value of the nut. Percentage kernel of 'Byrd' and 'Cunard' is higher than 'Pawnee', further increasing the value of the nut. Leaflet orientation of 'Cunard' leaves is similar to 'Pawnee', that is, the opposite leaflet is oriented at 180 degrees relative to each other whereas leaflets of most pecan genotypes droop to varying degrees, including 'Wichita'. The stigmatic surface of 'Cunard' is pale green in contrast to the ox-blood red stigmatic of 'Pawnee' and more like the green surface of 'Wichita'.

Table 1 below compares periods of stigma receptivity and pollen shedding of the 'Cunard' cultivar with these characteristics of a number of other cultivars.

TABLE 1

Approximate periods of pollen shedding and stigma receptivity for 'Cunard' and other cultivars, Albany, Georgia

| | Date | | | | | | | | | | | | | | | | | |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 |
| Protandrous cultivars | | | | | | | | | | | | | | | | | | |
| 'Cheyenne' | | | | ——— | ——— | ——— | ——— | ——— | ——— | ——— | ——— | ——— | ····· | ····· | ····· | ····· | ····· | ····· |
| 'Desirable' | | | | ——— | ——— | ——— | ——— | ——— | ——— | ——— | ——— | ——— | ——— | ····· | ····· | ····· | ····· | ····· |
| 'Pawnee' | | | | | | ——— | ——— | ——— | ——— | ——— | ——— | ——— | ····· | ····· | ····· | ····· | ····· | |

TABLE 1-continued

Approximate periods of pollen shedding and stigma receptivity for 'Cunard' and other cultivars, Albany, Georgia

| | Date | | | | | | | | | | | | | | | | | |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 |
| Protogynous cultivars | | | | | | | | | | | | | | | | | | |
| 'Cunard' (unpatented) | | | | | | ····· | ····· | ····· | ····· | ····· | ····· | ——— | ——— | ——— | ——— | ——— | ——— | ——— |
| 'Elliott' (unpatented) | | | | | | ····· | ····· | ····· | ····· | ····· | ····· | ····· | ····· | ——— | ——— | ——— | ——— | |
| 'Schley' (unpatented) | | | | | | ····· | ····· | ····· | ····· | ····· | ····· | ——— | ——— | ——— | ——— | ——— | ——— | |
| "Stuart' (unpatented) | | | | | | ····· | ····· | ····· | ····· | ····· | ····· | ····· | ····· | ····· | ····· | ····· | ····· | ····· |
| | | | | | | | | | | | | | | ——— | ——— | ——— | ——— | ——— |

····· = Period of stigma receptivity.
——— = Period of pollen shedding.

Tables 2 and 3 below compare the characteristics of nuts from 'Cunard' with nuts of other pecan varieties.

TABLE 2

Comparison of nut characteristics of 'Byrd', 'Pawnee', 'Cunard' and 'Stuart' pecan cultivars, Watkinsville, Georgia, 2000-2006.

| Cultivar | Wt./nut (g) | Nuts/lb. (no.) | Kernel (%) | Nut maturity date[z] |
|---|---|---|---|---|
| 'Byrd' | 7.4a | 61b | 62.2b | 9/22a |
| 'Pawnee' | 7.2b | 63b | 59.7c | 9/20a |
| 'Morrill' | 9.4a | 48a | 64.3a | 10/4c |
| 'Cunard' | 9.4a | 48a | 61.5b | 9/27b |
| 'Stuart' | 7.5b | 61b | 47.5d | 10/9d |

Means followed by the same letter within a column are not statistically different, $P \leq 0.05$, n = 7.
[z]Nut maturity date of 'Desirable' is 10/15.

TABLE 3

Nut characteristics of 'Byrd', 'Morrill', 'Desirable', and 'Cunard', Albany, Georgia 2006-2008.[z]

| Cultivar | Vol./nut (cc) | Wt./nut (g) | Nuts/lb. (no.) | Kernel (%) |
|---|---|---|---|---|
| 'Byrd' | 12.9b | 9.3b | 49b | 64.0b |
| 'Morrill' | 14.0b | 10.6a | 43a | 67.6a |
| 'Desirable' | 15.5a | 10.8a | 43a | 55.2c |
| 'Cunard' | 14.6b | 10.8a | 42a | 63.5b |

Means followed by the same letter within a column are not statistically different, $P \leq 0.05$, n = 7.
[z]Nut weight is greater and percentage kernel is higher than in Table 2 because of better irrigation.

Pecan nuts of large size that mature relatively early command a premium price. The price per pound normally declines as the harvest becomes later. Consequently, varieties that exhibit early maturity at harvest are commercially important. The color of a kernel's seed coat (lighter is preferred), and the percentage kernel of the nut also affects the selling price of pecans. Although the nut maturity of 'Cunard' is about 5 days later than nut maturity of 'Byrd', it is about 12 days earlier than the 'Stuart' cultivar and 23 days earlier than 'Desirable', and is well within the range of early market varieties. Although the nut maturity of 'Cunard' is later than 'Byrd', the maturity date is still early enough to be considered an early market variety.

As can be seen from Table 2, the weight per nut of 'Cunard' nuts are substantially the same as those of 'Morrill' and greater than the nut weight of 'Pawnee' and 'Byrd'. The percentage kernel of 'Cunard' nuts is high, but lower than 'Morrill'.

Table 4 below compares the susceptibility of 'Cunard' to kernel speckling with 'Byrd', 'Morrill' and 'Pawnee'.

TABLE 4

Susceptibility of 'Byrd', 'Morrill', 'Pawnee', and 'Cunard' to kernel speckling, Watkinsville, Georgia, 2000-2007, n = 8.

| Cultivar | No. of years with kernel speckling |
|---|---|
| 'Byrd' | 0 |
| 'Morrill' | 0 |
| 'Pawnee' | 4 |
| 'Cunard' | 0 |

Under stress, primarily fruiting stress, when 'Pawnee' cultivar pecan trees are grown in humid southeastern United States markets such as Georgia, the kernel seed coats of nuts develop conspicuous and unattractive dark spots. This speckling reduces the marketability of these nuts. Speckling has not been observed to be a problem of 'Cunard' nuts. In addition, unlike the 'Cunard' cultivar, during a heavy "on" nut production year for 'Pawnee' trees growing in Georgia, kernel development is relatively poor, resulting in a high percentage of the nuts being unmarketable or of reduced value.

Table 5 below compares the fruiting characteristics of 'Byrd', 'Morrill' and 'Cunard'.

TABLE 5

Fruiting characteristics of 'Byrd', 'Morrill' and 'Cunard' pecan trees, Albany, Georgia

| Cultivar | Years to fruiting[z] (no.) | Years until alternate bearing[z] (no.) |
|---|---|---|
| 'Byrd' | 2 | 3 |
| 'Morrill' | 2 | >5 |
| 'Cunard' | 2 | >5 |

[z]Years after topworking mature 'Kiowa' trees to the respective cultivar, n = 3.

As apparent from Table 5, 'Cunard' is precocious. 'Cunard', 'Morrill' and 'Byrd' each fruited two years after topworking onto older 'Kiowa' pecan trees. It does not appear the 'Cunard' is as precocious as 'Byrd' as indicated by the onset of alternate bearing in 'Byrd' trees the third year from topworking in contrast to alternate bearing in 'Cunard' trees having not yet occurred by the fifth year. Also, the original 'Cunard' tree bore its first fruit the eighth year from planting as seed. In comparison, the original tree of 'Byrd' first fruited the seventh year from planting as seed. The 'Morrill' tree had also not yet achieved alternate bearing by the fifth year. The 'Morrill' original tree bore its first fruit the tenth year from planting as seed.

As indicated in Table 6 below, the cluster size of 'Cunard' and 'Byrd' varieties are about the same. It does appear that 'Cunard' has lower density of fruiting shoots than 'Byrd'. Because of 'Cunard's precocity, large nut size and large cluster size, it is expected to bear alternately with increasing tree maturity as occurs with most pecan cultivars including its parent trees, 'Wichita' and 'Pawnee'.

TABLE 6

Fruit cluster size of 'Byrd', 'Desirable', 'Morrill', 'Pawnee' and 'Cunard', Watkinsville, Georgia.
Data are the average of three years 2005, 2006 and 2008.

| Cultivar | Fruit/cluster (no.) |
|---|---|
| 'Byrd' | 3.1d |
| 'Desirable' | 1.8a |
| 'Morrill' | 3.0cd |
| 'Pawnee' | 2.8b |
| 'Cunard' | 2.9bc |

Table 7 below compares leaf scab susceptibility of 'Byrd', 'Morrill', 'Desirable' and 'Cunard' in Leary and in Watkinsville, Ga. 'Pawnee' has been observed to be more susceptible to scab disease than 'Cunard' when grown in both locations, Georgia. The 'Wichita' pecan variety, when grown in Georgia's humid climate, is highly susceptible to scab fungus.

TABLE 7

Leaf scab susceptibility of 'Byrd', 'Desirable', 'Morrill' and 'Cunard', Leary and Watkinsville, Georgia.
Leaf scab[x]

| Cultivar | Leary, 2009[y] | Watkinsville, 2010[z] |
|---|---|---|
| 'Byrd' | 1.0a | 1.4b |
| 'Morrill' | 1.3ab | 2.0b |
| 'Cunard' | 1.2a | 1.8b |
| 'Desirable' | 4.7c | 3.8a |

Means followed by the same letter are not statistically different, P ≤ 0.05.
[x]1 = no scab lesions
2 = occasional lesion on leaf, less than 1% of leaves with lesions
3 = lesions scant on 2 to 10% of the leaves
4 = lesions widespread, but no leaf distortion
5 = lesions widespread and severe leaf distortions
[y]n = 19
[z]n = 5

TABLE 8

Leaf susceptibility of 'Byrd', 'Morrill', 'Cunard', and 'Desirable' to pecan leaf scorch mite, Graham Angus Pecan, Leary, Georgia, 2009.

| Cultivar | Leaf rating[z] |
|---|---|
| 'Byrd' | 1.1a |
| 'Morrill' | 1.1a |
| 'Cunard' | 2.2b |

Means followed by the same letter are not statistically different, P ≥ 0.05%, n = 19.
[z]1 = no damage
2 = trace
3 = multiple lesions
4 = minor defoliation
5 = severe defoliation

TABLE 9

Leaf susceptibility of 'Byrd', 'Morrill', 'Desirable' and 'Sumner' to black pecan aphids, Graham Angus Pecan, Leary, Georgia, 2009[y].

| Cultivar | Leaf rating[z] |
|---|---|
| 'Byrd' | 1.5c |
| 'Morrill' | 2.3b |
| 'Cunard' | 1.1d |
| 'Sumner' | 2.8a |

Means followed by the same letter are not statistically different, P ≥ 0.05%, n = 19.
[z]1 = no injury
2 = <1% of leaves with injury
3 = 1-10% of leaves with injury
4 = 11-50% of leaves with injury
5 = >50% of leaves with injury and partial defoliation

TABLE 10

Leaf susceptibility of 'Byrd', 'Morrill', 'Cunard' and 'Desirable' to N scorch[y], Graham Angus Pecan, Leary, Georgia, 2009.

| Cultivar | Leaf rating[z] |
|---|---|
| 'Byrd' | 1.2b |
| 'Morrill' | 1.5b |
| 'Cunard' | 1.1b |
| 'Desirable' | 4.7a |

Means followed by the same letter are not statistically different, P ≥ 0.05%, n = 19.

[z]1 = no scorch

2 = <1% of leaves with scorch

3 = 2-20%

4 = 21-40%

5 = ≥41%

In addition, under humid growing conditions in Georgia, Wichita fruit is highly susceptible to splitting (up to 75%) during the "water stage" (liquid endosperm stage) of fruit development. Fruit split occurs if rain and accompanying high humidity occurs at this stage. Although 'Wichita' has a relatively early nut maturity (7-10 days before 'Stuart') and acceptable nut size (57 nuts per pound), and a kernel percentage of 60-61%, which is higher than the 58-59% of 'Pawnee', because of the susceptibility to scab fungus and splitting it has become a less desirable variety for growing in Georgia. In some years, water split occurs in 'Cunard', but it has been less than 10 percent.

I claim:

1. A new and distinct variety of pecan tree, substantially as herein shown and described.

* * * * *

UNITED STATES PATENT AND TRADEMARK OFFICE

CERTIFICATE OF CORRECTION

PATENT NO. : PP24,373 P2
APPLICATION NO. : 13/199810
DATED : April 8, 2014
INVENTOR(S) : Sparks It is certified that error appears in the above-identified patent and that said Letters Patent is hereby corrected as shown below:

In the Specification:

Replace Table 1 beginning at Column 5, line 52 - Column 6, line 24, with the following Table 1:

Table 1 below compares periods of stigma receptivity and pollen shedding of the 'Cunard' cultivar with these characteristics of a number of other cultivars.

Table 1. Approximate periods of pollen shedding and stigma receptivity for 'Cunard' and other cultivars, Albany, Georgia

| | Date | | | | | | | | | | | | | | | | | |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 |
| Protandrous cultivars | | | | | | | | | | | | | | | | | | |
| 'Cheyenne' | | | | _____ | | | | | | | | ..... | | | | | | |
| 'Desirable' | | | _____ | | | | | | | | | | ..... | | | | | |
| 'Pawnee' | | | | | _____ | | | | | | | | ..... | | | | | |
| Protogynous cultivars | | | | | | | | | | | | | | | | | | |
| 'Cunard' (unpatented) | | | | ..... | | | | | | | | _____ | | | | | | |
| 'Elliott' (unpatented) | | | | | ..... | | | | | | | | _____ | | | | | |
| 'Schley' (unpatented) | | | | | ..... | | | | | | | _____ | | | | | | |
| "Stuart' (unpatented) | | | | | ..... | | | | | | | | | _____ | | | | |

..... = Period of stigma receptivity.

_____ = Period of pollen shedding.

Signed and Sealed this
Twelfth Day of May, 2015

Michelle K. Lee

Michelle K. Lee
*Director of the United States Patent and Trademark Office*